United States Patent
Boulnois et al.

(10) Patent No.: US 9,023,079 B2
(45) Date of Patent: May 5, 2015

(54) FENESTRATED SUPER ATRAUMATIC GRASPER APPARATUS

(75) Inventors: Jean-Luc Boulnois, Boston, MA (US); Richard C. Kowalski, Hampton, NH (US)

(73) Assignee: Microline Surgical, Inc., Beverly, MA (US)

( * ) Notice: Subject to any disclaimer, the term of this patent is extended or adjusted under 35 U.S.C. 154(b) by 315 days.

(21) Appl. No.: 13/542,900

(22) Filed: Jul. 6, 2012

(65) Prior Publication Data

US 2013/0012985 A1   Jan. 10, 2013

Related U.S. Application Data

(63) Continuation of application No. 11/941,298, filed on Nov. 16, 2007, now Pat. No. 8,252,021.

(51) Int. Cl.
| | |
|---|---|
| *A61B 17/00* | (2006.01) |
| *A61B 17/29* | (2006.01) |
| *A61B 17/28* | (2006.01) |

(52) U.S. Cl.
CPC ............... *A61B 17/29* (2013.01); *A61B 17/282* (2013.01); *A61B 2017/2825* (2013.01); *A61B 2017/2926* (2013.01)

(58) Field of Classification Search
USPC ......... 606/205–207; 81/418, 419, 424.5, 426, 81/426.5
See application file for complete search history.

(56) References Cited

U.S. PATENT DOCUMENTS

| | | | |
|---|---|---|---|
| 3,503,396 A | 3/1970 | Pierie et al. | |
| 5,690,269 A | 11/1997 | Bolanos et al. | |
| 5,728,121 A | 3/1998 | Bimbo et al. | |
| 5,964,779 A | 10/1999 | Mayenberger et al. | |
| 6,099,550 A * | 8/2000 | Yoon | 606/205 |
| 6,228,083 B1 | 5/2001 | Lands et al. | |
| 6,238,414 B1 | 5/2001 | Griffiths | |
| 6,558,408 B1 | 5/2003 | Fogarty et al. | |
| 6,579,304 B1 * | 6/2003 | Hart et al. | 606/207 |
| 6,656,193 B2 | 12/2003 | Grant et al. | |
| 7,182,775 B2 | 2/2007 | De Guillebon et al. | |
| 7,264,623 B2 * | 9/2007 | Harris et al. | 606/148 |
| 2003/0191465 A1 | 10/2003 | Yahagi et al. | |
| 2004/0172057 A1 * | 9/2004 | Guillebon et al. | 606/207 |
| 2008/0009900 A1 * | 1/2008 | Heaven et al. | 606/207 |

* cited by examiner

*Primary Examiner* — Victor Nguyen
*Assistant Examiner* — Kevin Everage
(74) *Attorney, Agent, or Firm* — Greenblum & Bernstein P.L.C.

(57) ABSTRACT

A surgical tool assembly includes a pair of opposing jaws. Further, a viewing opening may be provided in at least one of the opposing jaws. The viewing opening may extend from an upper to a lower surface of the opposing jaw in which the viewing opening is provided. The viewing opening may include a material retainer provided proximate the lower surface of the opposing jaw in which the viewing opening is provided. The material retainer may include an inclined surface inclined towards a central axis of the viewing opening. A grasping insert may be molded onto a lower surface of the opposing jaw in which the viewing opening is provided and an elastomeric material of the grasping inserts may within the viewing opening, the material of the grasping inserts covering the inclined surface of the first material retainer.

20 Claims, 4 Drawing Sheets

FENESTRATED SUPER ATRAUMATIC GRASPER APPARATUS

CROSS-REFERENCE RELATED APPLICATION

The present application is a continuation of U.S. application Ser. No. 11/941,298, filed Nov. 16, 2007, the disclosures of which are incorporated herein by reference in its entirety.

BACKGROUND OF THE INVENTION

I. Field of the Invention

The present invention relates generally to a surgical tool assembly including a pair of opposing jaws.

II. Discussion of the Background Art

In the conventional art, a surgical tool assembly having a pair of opposing jaws and corresponding inserts is known. For example, a pair of opposing jaws of the conventional tool assembly may include inserts having projections provided on an attachment surface and a pair of opposing jaws having corresponding holes provided on a jaw surface which engages the attachment surface of a corresponding insert. In this regard, the projections and holes may be configured to have a snap-fit relationship which facilities removable attachment of the insert to the jaw.

Further, in another exemplary embodiment of the conventional art surgical tool assembly, a bottom surface of the insert may simply be provided with an adhesive and adhered to a corresponding surface of an opposing jaw.

However, each of the above-mentioned constructions have at least the disadvantages of the insert being prone to unintentional separation from the corresponding jaw, e.g., when the surgical tool is in use or being transported. Further, even when the insert is not completely separated from the jaw, the positioning of the insert may be compromised. For example, the orientation of opposing inserts may become misaligned with respect to each other, thereby diminishing the reliability, gasping efficiency and accuracy of the surgical tool.

Further, in each of the above-mentioned conventional art surgical tools, the surgical tools are not provided with an opening for viewing tissue, which may be grasped by the pair of opposing jaws, because the mechanisms for coupling the inserts to the opposing jaw are generally provided on a bottom surface of the insert and an opposing surface of the jaw, thereby preventing a viewing opening from being provided in both the insert and corresponding jaw.

Also, in each of the above-mentioned conventional art surgical tools, the reliability of an insert connected to a corresponding jaw would be compromised if either one of the conventional art surgical tools was provided with a viewing opening (or fenestration).

More specifically, in the conventional tool assembly including inserts having projections provided on an attachment surface and a pair of opposing jaws having corresponding holes, such a viewing opening would decrease a surface area provided on an attachment surface; and would require omitting the projections and openings from an area of the insert and jaw which is occupied with a viewing opening thereby decreasing the durability and reliability of the surgical tool assembly.

Further, in the conventional tool assembly where a bottom surface of the insert is merely provided with an adhesive and adhered to a corresponding surface of an opposing jaw, such a viewing opening would decrease a surface area which may have an adhesive attached thereto. In other words, no adhesive can be applied to an area of the insert and jaw which is occupied with a viewing opening; thus, the durability and reliability of the surgical tool assembly is compromised.

SUMMARY OF THE INVENTION

Accordingly, a non-limiting embodiment of the present invention provides a surgical tool assembly including a pair of opposing jaws pivotally connected to each other. Further, at least one viewing opening (e.g., an elongated slot or other suitable fenestration) may be provided in at least one of the opposing jaws. The at least one viewing opening may extend through an upper to a lower surface of the opposing jaw in which the viewing opening is provided. Additionally, the at least one viewing opening may include a material retainer provided at the lower surface of the opposing jaw in which the at least one viewing opening is provided. Further, the material retainer may include an inclined surface inclined towards the at least one viewing opening.

Additionally, an elastomeric grasping insert may be molded onto a lower surface of the opposing jaw in which the viewing opening is provided. In this regard, a material of the grasping insert may extend within the at least one viewing opening so as to cover the inclined surface of the material retainer.

Further, in accordance with an additional feature, the at least one viewing opening may include a lower surface defined by the at least one viewing opening. Additionally, at least a portion of the inclined surface of the material retainer may generally extend about the lower surface.

Further, the at least one viewing opening may include first and second viewing openings. In this regard, the first viewing opening may be provided in one of the opposing jaws and the second viewing opening may be provided in the other of the opposing jaws.

In an additional non-limiting feature, the material retainer may include first and second material retainers (or distal material retainer). In this regard, the second material retainer may be provided at a distal end of the opposing jaw in which the at least one viewing opening is provided. Further, the second material retainer may include a generally curved arcuate surface and a sloped surface extending from the arcuate surface towards a lower surface of the opposing jaw in which the at least one viewing opening is provided. In this regard, the material of the grasping insert may cover the sloped surface of the second material retainer.

In yet another non-limiting embodiment, the opposing jaw in which the at least one viewing opening is provided may include a first channel extending at a distal end of the at least one viewing opening. Further, a second channel, extending at a proximal end of the at least one viewing opening, may be provided. Further, the material of the grasping insert may extend within the first and second channels.

Additionally, the inclined surface of the first material retainer may be roughened. Further, an inner circumferential surface of the at least one viewing opening may also be roughened, as well as corresponding surfaces of the first and second channels.

According to another feature, a lower surface of the grasping insert may have a plurality of teeth.

In another non-limiting feature, the first channel may have a first end, a second end, and a bottom surface. In this regard, the bottom surface of the first channel may be inclined and extend between the first and second ends of the first channel such that a depth of the first channel increases towards the first end of the first channel.

Further, the second channel may have a first end, a second end, and a bottom surface. In this regard, the bottom surface of the second channel may be inclined and extend between the first and second ends of the second channel such that a depth of the second channel increases towards the second end of the second channel.

According to another non-limiting feature of the present invention, the at least one viewing opening, the first channel, and the second channel may define a continuous path. In this regard, the material of the grasping insert may extend within the continuous path.

Further, in another non-limiting feature of the present invention the surgical tool assembly may include a pair of opposing jaws pivotally connected to each other. In this regard, at least one viewing opening may be provided in at least one of the opposing jaws, the at least one viewing opening may extend through an upper to a lower surface of the opposing jaw in which the viewing opening is provided. Additionally, at least one distal material retainer may be provided at a distal end of the opposing jaw in which the at least one viewing opening is provided. Further, the at least one distal material retainer may include a generally curved arcuate surface and a sloped surface extending from the arcuate surface towards a lower surface of the opposing jaw in which the at least one viewing opening is provided. Further, an elastomeric grasping insert may be molded onto a lower surface of the opposing jaw in which the viewing opening is provided, wherein a material of the grasping inserts covers the sloped surface of the at least one forward material retainer.

Additionally, the opposing jaw in which the at least one viewing opening is provided may include a first channel extending axially at the lower surface of the opposing jaw in which the at least one viewing opening is provided and provided at a front end of the at least one viewing opening, and a second channel extending axially at the lower surface of the opposing jaw in which the at least one viewing opening is provided and provided at a proximal end of the at least one viewing opening. In this regard, the material of the grasping insert extends within the first and second channels.

Further, the at least one distal material retainer may include first and second distal material retainers. In this regard, the first distal material retainer may be provided on one of the opposing jaws and the second distal material retainer may be provided on the other of the opposing jaws.

BRIEF DESCRIPTION OF THE DRAWINGS

The present invention is further described in the detail description which follows, in reference to the noted plurality of drawings, by way of non-limiting examples of preferred embodiments of the present invention, in which like characters represent like elements throughout the several views of the drawings, and wherein.

DETAILED DESCRIPTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Figure 1:
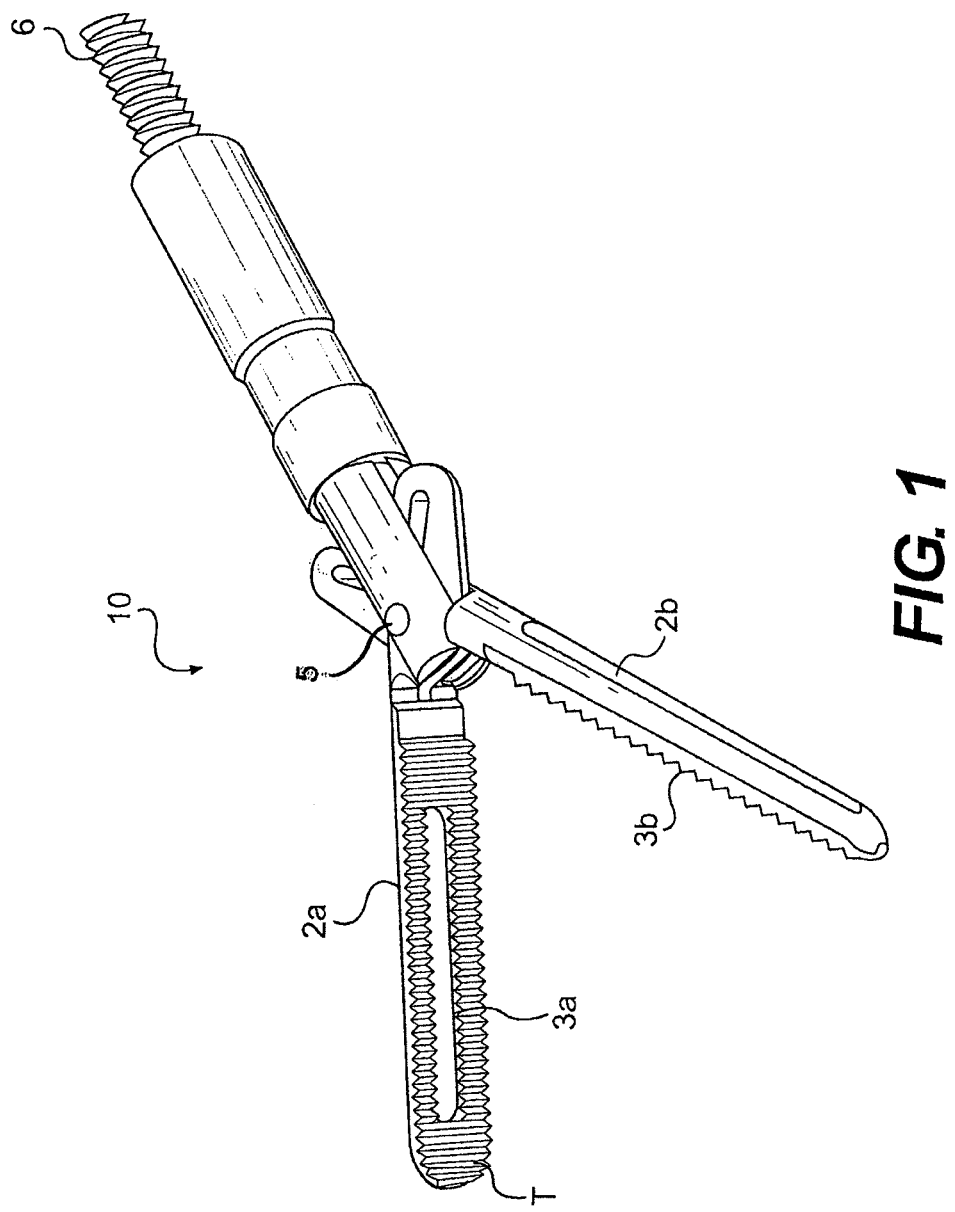
FIG. 1 is a perspective view of a surgical tool assembly according to a non-limiting embodiment of the present invention, including opposing jaws having corresponding grasping inserts molded thereon.
Figure 2:
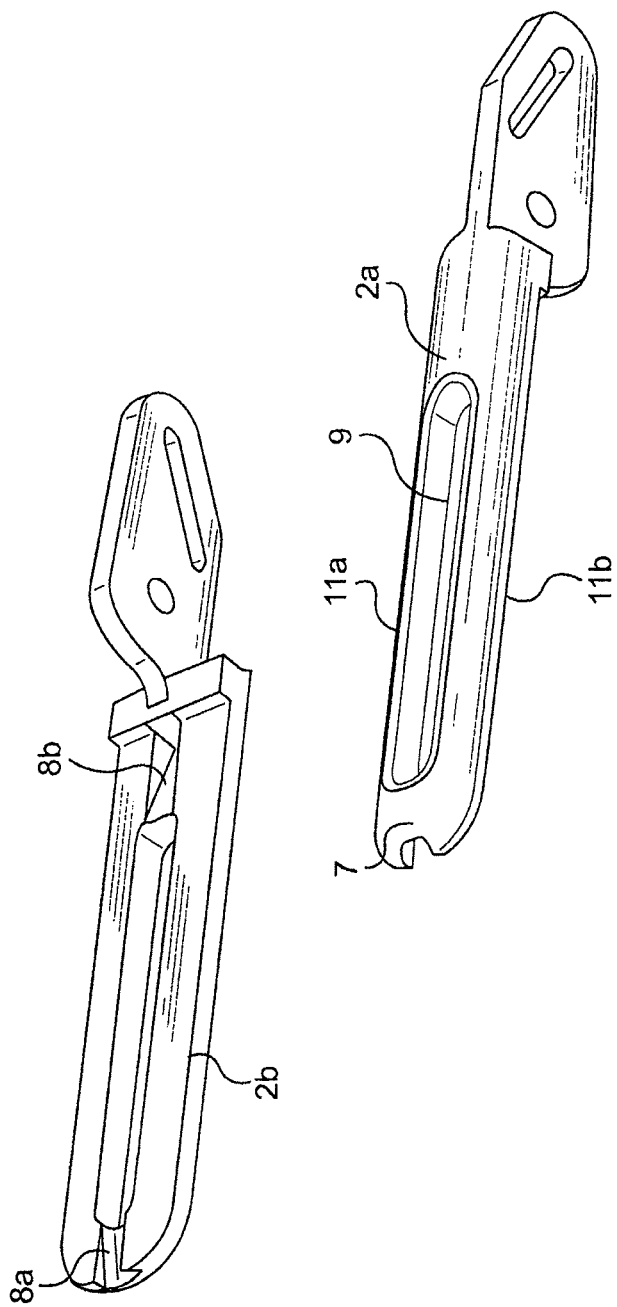
FIG. 2 is an exploded view of a pair of opposing jaws according to a non-limiting embodiment of the present invention without the grasping insert.

Referring to the drawings, FIG. 1 shows a perspective view of a pair of opposing jaws 2a and 2b (i.e., of a surgical tool assembly) according to a non-limiting embodiment of the present invention and FIG. 2 shows a perspective view of the jaws in a spaced relation. In this regard, the pair of opposing jaws 2a and 2b may be pivotally connected by, e.g., a pin 5 to each other. Additionally, at least one fenestrated viewing opening 9 is provided in at least one of the opposing jaws 2a and 2b.

Figure 7:
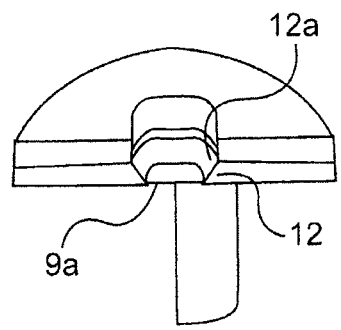
FIG. 7 is a cross-sectional view of one of the pair of opposing jaws of FIG. 4 showing a rear end of the opposing jaw taken along section B-B of FIG. 4 without the grasping insert.

For example, the at least one viewing opening 9 may extend from an upper 11a to a lower 11b surface of the opposing jaw 2a or 2b in which the viewing opening 9 is provided, as illustrated in FIG. 2. Further, and as illustrated in FIG. 7, the at least one viewing opening 9 may include a first material retainer 12 provided proximate the lower surface 9a of the opposing jaw 2a or 2b in which the at least one viewing opening 9 is provided. Further, the first material retainer 12 may include an inclined surface 12a inclined towards the at least one viewing opening 9.

Additionally, referring again to FIG. 1, a grasping insert 3a or 3b is molded onto a lower surface of the opposing jaw 2a or 2b in which the viewing opening 9 is provided. In this regard, a material of the grasping insert 3a or 3b may extend within the at least one viewing opening 9 so as to cover the inclined surface 12a of the first material retainer 12, such that the first material retainer substantially prevents the insert from slipping off the jaw 2a, 2b. In this regard, the inclined surface 12a provides further retentions, i.e., because the inclined surface 12a is covered by the elastomeric over mold material; thus, slippage of an insert 3a or 3b with respect to a corresponding jaw 2a, 2b is further prevented.

Further, as shown in FIG. 7, and in accordance with an additional feature, the at least one viewing opening 9 may unitarily include a surface opening 9a defined by the at least one viewing opening 9. Additionally, at least a portion of the inclined surface 12a of the first material retainer 12 may generally extend about the lower surface 9a. However, one of ordinary skill in the art would appreciate that the first material retainer 12 may be provided in a variety of forms. For example, the first material retainer 12 may have a curved surface; the first material retainer 12 may extend continuously or discontinuously around the lower opening; or the first material retainer may includes a plurality of inclined surfaces spaced at regular or irregular intervals and extend about the lower opening 9a.

Further, the at least one viewing opening 9 may include first and second viewing openings 9 (i.e., provided in each of the opposing jaws 2a and 2b). In this regard, the first viewing opening 9 may be provided in one of the opposing jaws 2a, 2b and the second viewing opening 9 may be provided in the other of the opposing jaws 2a, 2b.

Figure 3:
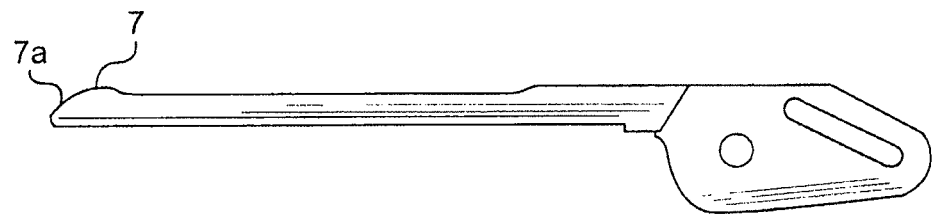
FIG. 3 is a side view of one of the pair of opposing jaws according to the non-limiting embodiment of FIG. 2 without the grasping insert.

Referring to FIG. 3, a second material retainer 7 (or distal material retainer) may be unitarily provided at a distal end of the opposing jaw 2a, 2b in which the at least one viewing opening 9 is provided. Further, the second material 7 retainer may include a generally curved arcuate surface 7b and a sloped surface 7a extending (along a separate line) from the arcuate surface 7b towards a lower surface 11a of the opposing jaw 2a, 2b in which the at least one viewing opening 9 is provided. In this regard, the material of the grasping insert 3a, 3b may cover the sloped surface 7a of the second material retainer 7, such that the second material retainer substantially prevents the insert from slipping off the jaw 2a, 2b. More specifically, the sloped surface 7a of the second material retainer is angle such that engagement between the elastomeric material and sloped surface 7a prevents slippage of the grasping insert 3a, 3b off the jaw 2a, 2b.

Figure 4:
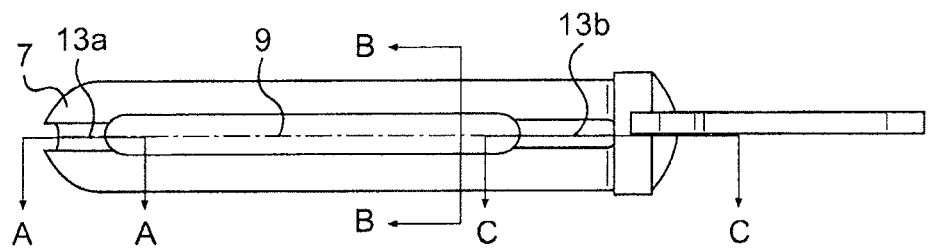
FIG. 4 is a top plan view of one of the pair of opposing jaws according to the non-limiting embodiment of FIG. 2 without the grasping insert.
Figure 5:
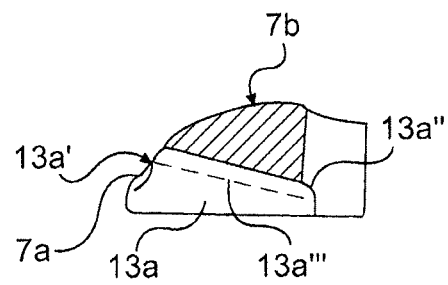
FIG. 5 is a cross-sectional view of one of the pair of opposing jaws of FIG. 4 showing a front end of the opposing jaw taken along section A-A of FIG. 4 without the grasping insert.
Figure 6:
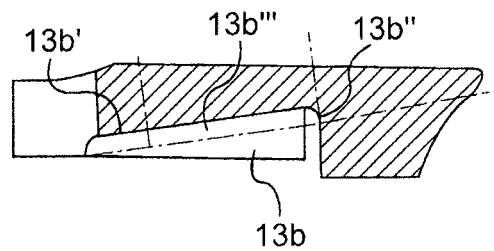
FIG. 6 is a cross-sectional view of one of the pair of opposing jaws of FIG. 4 showing a rear end of the opposing jaw taken along section C-C of FIG. 4 without the grasping insert.

According to another feature, as illustrated in FIGS. 4-6, the opposing jaw 2a or 2b in which the at least one viewing opening 9 is provided may include a first channel 13a axially extending lower surface 11a of the opposing jaw in which the at least one viewing opening 9 is provided and provided at a front end of the at least one viewing opening 9, and a second channel 13b recessed upwardly from the lower surface 11a of the opposing jaw 2a or 2b in which the at least one viewing opening 9 is provided and provided at a rear end of the at least one viewing opening 9. In this regard, the material of the grasping insert may extend within the first 13a and second 13b channels, thereby providing further retention of the elastomeric material. For example, positioning the first 13a and second 13b channels at opposing sides of the viewing opening provides further retention of the elastomeric material along generally an entire length of the grasping insert 3a, 3b; thus, durability and integrity of the surgical tool is improved.

Additionally, the inclined surface 12a of the first material retainer 12 may be roughened, e.g., including but not limited to knurled, scored, abraded, and the like. For example, a surface of the first material retainer 12a may be provided with intricacies to increase the surface area thereof which allow for further retention of the molded material on the first material retainer 12. Thus, one of ordinary skill in the art would recognize that an inner circumferential surface of the at least one viewing opening 9 may be roughened, in addition to or alternatively to corresponding surfaces of the first 13a and second 13b channels.

According to another feature, as illustrated in FIG. 1, a lower surface of the grasping insert 3a may have a plurality of teeth T. However, one of ordinary skill in the art would recognize that the lower surface of the grasping insert 3a may be provided with various engagement surfaces without departing from the spirit and scope of the present invention. For example, the lower surface of the grasping insert 3a may be provided with dimples or protrusions suitable for grasping tissue.

Referring to FIG. 5, the first channel 13a may have a first end 13a', a second end 13a", and a bottom surface 13a'". In this regard, the bottom surface 13a'" of the first channel 13a may be inclined and extend between the first 13a' and second 13a" ends of the first 13a channel such that a depth of the first 13a channel increases towards the first end 13a' of the first channel 13a.

Referring to FIG. 6, the second channel 13b may have a first end 13b', a second end 13b", and a bottom surface 13b'". In this regard, the bottom surface 13b'" of the second channel 13b may be inclined and extend between the first 13b' and second ends 13b" of the second channel 13b such that a depth of the second channel 13b increases towards the second end 13b" of the second channel 13b.

In this regard, an increasing depth of the first 13a and second 13b channels further improves retention of a corresponding grasping insert 3a because engagement between the elastomeric material of the grasping insert 3a and the first 13a and second 13b channels are increased. Thus, retention of the grasping inserts 3a, 3b on a corresponding jaw 2a, 2b is improved at the distal and proximate ends of a corresponding jaw 2a, 2b.

According to another non-limiting feature of the present invention, the at least one viewing opening 9, the first channel 13a, and the second channel 13b may define a continuous path (as shown in FIG. 4). In this regard, the material of the grasping insert 3a or 3b may extend within the continuous path, thereby improving retention of the grasping insert along generally an entire length of the corresponding jaw 2a, 2b.

Further, one of ordinary skill in the art would appreciate that it is possible to provide the first 12 and second 7 material retainers on at least one of the opposing jaws 2a, 2b in any suitable combination. For example, one or both of the pair of opposing jaws 2a and 2b may only be provided with either one of the first material retainer 12 or the second 7 material retainer. In other words, the first 12 and second 7 material retainers of the present invention may be used separately or in combination with each other without departing from the scope of the present invention.

Further, it should be appreciated that the recitations of upper and lower and the present disclosure are only being used to facilitate understanding of the present application. In this regard, one of ordinary skill in the art would readily understand that the orientations of opposing jaw elements, when pivotably coupled to one another, may be opposite each other.

It is further noted that the foregoing examples have been provided merely for the purpose of explanation and are in no way to be construed as limiting of the present invention. While the present invention has been described with reference to a preferred embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A surgical tool assembly, comprising:
a pair of opposing jaws pivotally connected to each other;
at least one viewing opening provided in at least one of the opposing jaws, the at least one viewing opening penetrating through an upper and lower surface of the opposing jaw in which the viewing opening is provided, the at least one viewing opening having a width defined in a direction extending between side surfaces of the opposing jaw in which the viewing opening is provided, the at least one viewing opening having a material retainer provided at the lower surface of the opposing jaw in which the at least one viewing opening is provided, the material retainer comprising an inclined surface inclined towards the at least one viewing opening such that the width of the at least one viewing opening decreases at the lower surface of the opposing jaw in which the at least one viewing opening is provided, and the material retainer being positioned at an inner periphery of the at least one viewing opening, the inclined surface of the material retainer extending around the inner periphery of the at least one viewing opening; and an elastomeric grasping insert molded onto the lower surface of the opposing jaw in which the viewing opening is provided, wherein a material of the grasping inserts extends within the at least one viewing opening and covers the inclined surface of the material retainer.

2. The surgical tool assembly according to claim 1, wherein the at least one viewing opening further comprises a lower surface defined by the at least one viewing opening, wherein at least a portion of the inclined surface of the material retainer generally extends about the lower surface.

3. The surgical tool assembly according to claim 2, wherein the at least one viewing opening comprises first and second viewing openings, the first viewing opening being provided in one of the opposing jaws and the second viewing opening being provided in the other of the opposing jaws.

4. The surgical tool assembly according to claim 1, wherein the at least one viewing opening comprises first and second viewing openings, the first viewing opening being provided in one of the opposing jaws and the second viewing opening being provided in the other of the opposing jaws.

5. The surgical tool assembly according to claim 1, wherein the material retainer is a first material retainer, the surgical tool assembly further comprising a second material retainer provided at a distal end of the opposing jaw in which the at least one viewing opening is provided, the second material retainer comprising a generally curved arcuate surface and a sloped surface extending from the arcuate surface towards a lower surface of the opposing jaw in which the at least one viewing opening is provided, the material of the grasping insert covering the sloped surface of the second material retainer.

6. The surgical tool assembly according to claim 1, wherein the opposing jaw in which the at least one viewing opening is provided comprises:
a first channel axially extending at a distal end of the at least one viewing opening;
a second channel axially extending at a proximal end of the at least one viewing opening; and
wherein the material of the grasping insert extends within the first and second channels.

7. The surgical tool assembly according to claim 6, wherein corresponding surfaces of the first and second channels are roughened.

8. The surgical tool assembly according to claim 6, wherein the first channel has a first end, a second end, and a bottom surface, the bottom surface of the first channel being inclined and extending between the first and second ends of the first channel such that a depth of the first channel increases towards the first end of the first channel.

9. The surgical tool assembly according to claim 8, wherein the second channel has a first end, a second end, and a bottom surface, the bottom surface of the second channel being inclined and extending between the first and second ends of the second channel such that a depth of the second channel increases towards the second end of the second channel.

10. The surgical tool assembly according to claim 6, wherein the second channel has a first end, a second end, and a bottom surface, the bottom surface of the second channel being inclined and extending between the first and second ends of the second channel such that a depth of the second channel increases towards the second end of the second channel.

11. The surgical tool assembly according to claim 1, wherein the inclined surface is roughened.

12. The surgical tool assembly according to claim 1, wherein an inner circumferential surface of the at least one viewing opening is roughened.

13. The surgical tool assembly according to claim 1, wherein a lower surface of the grasping insert comprises a plurality of teeth.

14. The surgical tool assembly according to claim 1, the grasping insert being provided about a periphery of the at least one viewing opening.

15. The surgical tool assembly according to claim 1, the material retainer extending about the at least one viewing opening.

16. A surgical tool assembly comprising:
a pair of opposing jaws pivotally connected to each other;
at least one viewing opening provided in at least one of the opposing jaws, the at least one viewing opening penetrating through an upper and a lower surface of the opposing jaw in which the viewing opening is provided, the at least one viewing opening having a width defined in a direction extending between side surfaces of the opposing jaw in which the viewing opening is provided;
an elastomeric grasping insert molded onto the lower surface of the opposing jaw in which the viewing opening is provided;
a first material retainer positioned at an inner periphery of the at least one viewing opening such that the width of the at least one viewing opening decreases at the outer surface of the opposing jaw in which the at least one viewing opening is provided, the first material retainer having an inclined surface extending around the inner periphery of the at least one viewing opening; and
at least one second material retainer provided at a distal end of the opposing jaw in which the at least one viewing opening is provided, the at least one second material retainer comprising a generally curved arcuate surface and a sloped surface extending from the arcuate surface towards the lower surface of the opposing jaw in which the at least one viewing opening is provided, the material of the grasping insert covering the sloped surface of the at least one second material retainer.

17. The surgical tool assembly according to claim 16, wherein the opposing jaw in which the at least one viewing opening is provided comprises:
a first channel axially extending at a distal end of the at least one viewing opening;
a second channel axially extending at a proximal end of the at least one viewing opening; and
wherein the material of the grasping insert extends within the first and second channels.

18. The surgical tool assembly according to claim 16, wherein the at least one second material retainer comprises first and second forward material retainers, the first forward material retainer being provided in one of the opposing jaws and the second forward material retainer being provided in the other of the opposing jaws.

19. The surgical tool assembly according to claim 16, the grasping insert being provided about a periphery of the at least one viewing opening.

20. The surgical tool assembly according to claim 16, the material retainer extending about the at least one viewing opening.

* * * * *